(12) United States Patent
Davis et al.

(10) Patent No.: US 12,220,488 B2
(45) Date of Patent: *Feb. 11, 2025

(54) CANNABINOID DOSAGE FORMS

(71) Applicant: TGC Network LLC, Alamosa, CO (US)

(72) Inventors: Justin Davis, Alamosa, CO (US); Richard P. Baker, Anaheim, CA (US)

(73) Assignee: TGC Network LLC, Saguache, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/531,430

(22) Filed: Nov. 19, 2021

(65) Prior Publication Data

US 2022/0071910 A1  Mar. 10, 2022

Related U.S. Application Data

(63) Continuation of application No. 16/230,507, filed on Dec. 21, 2018, now Pat. No. 11,179,340.

(60) Provisional application No. 62/612,172, filed on Dec. 29, 2017.

(51) Int. Cl.
  *A61K 9/20* (2006.01)
  *A61K 31/05* (2006.01)

(52) U.S. Cl.
  CPC .......... *A61K 9/2095* (2013.01); *A61K 9/2077* (2013.01); *A61K 31/05* (2013.01); *A61K 9/2009* (2013.01); *A61K 9/2031* (2013.01); *A61K 9/2054* (2013.01); *A61K 9/2059* (2013.01)

(58) Field of Classification Search
  CPC .................. A61K 9/20; A61K 31/05
  See application file for complete search history.

(56) References Cited

U.S. PATENT DOCUMENTS

| 9,044,390 | B1 | 6/2015 | Speier |
| 9,186,386 | B2 | 11/2015 | Speier |
| 10,092,855 | B2 | 10/2018 | Chess |
| 11,179,340 | B2* | 11/2021 | Davis ...................... A61K 31/05 |
| 2007/0072939 | A1* | 3/2007 | Kupper .................... A61P 25/16 514/454 |
| 2016/0143972 | A1* | 5/2016 | Stebbins .............. A61K 36/185 424/725 |
| 2016/0228385 | A1* | 8/2016 | Sievers ................... A61P 35/00 |
| 2016/0279077 | A1 | 9/2016 | De Vries et al. |
| 2017/0349518 | A1* | 12/2017 | Dickman ................. C07C 39/23 |
| 2019/0110981 | A1* | 4/2019 | Weimann ............. A61K 9/0014 |

FOREIGN PATENT DOCUMENTS

| EP | 3274321 | 1/2018 |
| WO | 2015/065179 | 5/2015 |
| WO | 2016/153347 | 9/2016 |

OTHER PUBLICATIONS

LFA Tablet Pressers. Tdp 5 Desktop Tablet Press: User Manual. LFA Machines Oxford Ltd., https://lfa-lfamachinesoxfor.netdna-ssl.com/media/contenttype/documents/TDP-5-Manual.pdf, originally downloaded Nov. 8, 2018, 8 pages.

Morales et al. An Overview on Medicinal Chemistry of Synthetic and Natural Derivatives of Cannabidiol. Frontiers in Pharmacology [Internet], Jun. 2017, 8:422, https://doi.org/10.3389/fphar.2017.00422/full.

PCT International Patent Application No. PCT/US18/67962, Invitation to Pay Additional Fees dated Mar. 4, 2019, 2 pages.

U.S. Appl. No. 62/612,172, filed Dec. 29, 2017.
U.S. Appl. No. 16/230,507, Office Action mailed Mar. 17, 2020.
U.S. Appl. No. 16/230,507, Office Action mailed Sep. 28, 2020.
U.S. Appl. No. 16/230,507, Office Action mailed Jan. 13, 2021.

* cited by examiner

*Primary Examiner* — Michael B. Pallay

(74) *Attorney, Agent, or Firm* — Craig R. Miles; CR MILES P.C.

(57) ABSTRACT

A dosage form containing an amount of cannabidiol pressed into a tablet.

8 Claims, 3 Drawing Sheets

CANNABINOID DOSAGE FORMS

This United States Patent Application is a continuation of U.S. patent application Ser. No. 16/230,507, filed Dec. 21, 2018, now U.S. Pat. No. 11,179,340, issued Nov. 23, 2021, which claims the benefit of U.S. Provisional Patent Application No. 62/612,172, filed Dec. 29, 2017, each hereby incorporated by reference herein.

This United States Non-Provisional Patent Application claims the benefit of U.S. Provisional Patent Application No. 62/612,172, filed Dec. 29, 2017, hereby incorporated by reference herein.

I. FIELD OF THE INVENTION

Generally, a dosage form including an amount of cannabinoid pressed into a tablet. In particular, a dosage form including an amount of cannabidiol pressed into a tablet.

II. SUMMARY OF THE INVENTION

Accordingly, a broad object of particular embodiments of the invention can be to provide a dosage form comprising, consisting essentially of, or consisting of one or more cannabinoids pressed into a tablet. The amount of cannabinoid can have a pre-selected purity and pre-selected particle size distribution range which permits the cannabinoid, or combination of cannabinoids, to be pressed into a tablet, and, in particular embodiments, without the use of any flow agent or binder agent admixed with the amount of cannabinoid to be pressed into a tablet.

Another broad object of particular embodiments of the invention can be to provide a dosage form comprising, consisting essentially of, or consisting of an amount of cannabidiol pressed into a tablet. The amount of cannabidiol can have a pre-selected purity and pre-selected particle size distribution range which permits the amount of cannabidiol to be pressed into a tablet, and in particular embodiments, pressed into a tablet without the use of any flow agent or binder agent admixed with the amount of cannabidiol to be pressed into a tablet.

Another broad object of particular embodiments of the invention can be to provide a method of making a dosage form including an amount of cannabinoid such as cannabidiol, pressed into a tablet, the method including one or more of: disposing an amount of cannabinoid, such as cannabidiol, in a pill press and operating the pill press to form cannabinoid tablets such as cannabidiol tablets. Embodiments of the method can further include pre-selecting a purity or pre-selecting a particle size distribution range of crystalline cannabinoid such as crystalline cannabidiol, or combinations of crystalline cannabinoids, or derivatives thereof, which permit a cannabinoid such as cannabidiol to be pressed into a tablet, and, in particular embodiments, without the use of any flow agent or binder agent admixed with the amount of cannabinoid to be pressed into a tablet. Particular embodiments can further include weighing the tablets, and determining the average amount of cannabinoid, such as cannabidiol, contained in each of the tablets.

Another broad object of particular embodiments can be to provide a method of using a cannabinoid tablet, the method including one or more of obtaining one or more tablets having an amount of cannabidiol having a purity and a tablet weight, determining the amount of cannabidiol in the one or more tablets, determining a dosage of the amount of cannabidiol, selecting one or more tablets corresponding to the dosage, and consuming one or more tablets corresponding to the dosage.

Naturally, further objects of the invention are disclosed throughout other areas of the specification, drawings, photographs, and claims.

IV. DETAILED DESCRIPTION OF THE INVENTION

Figure 1A:
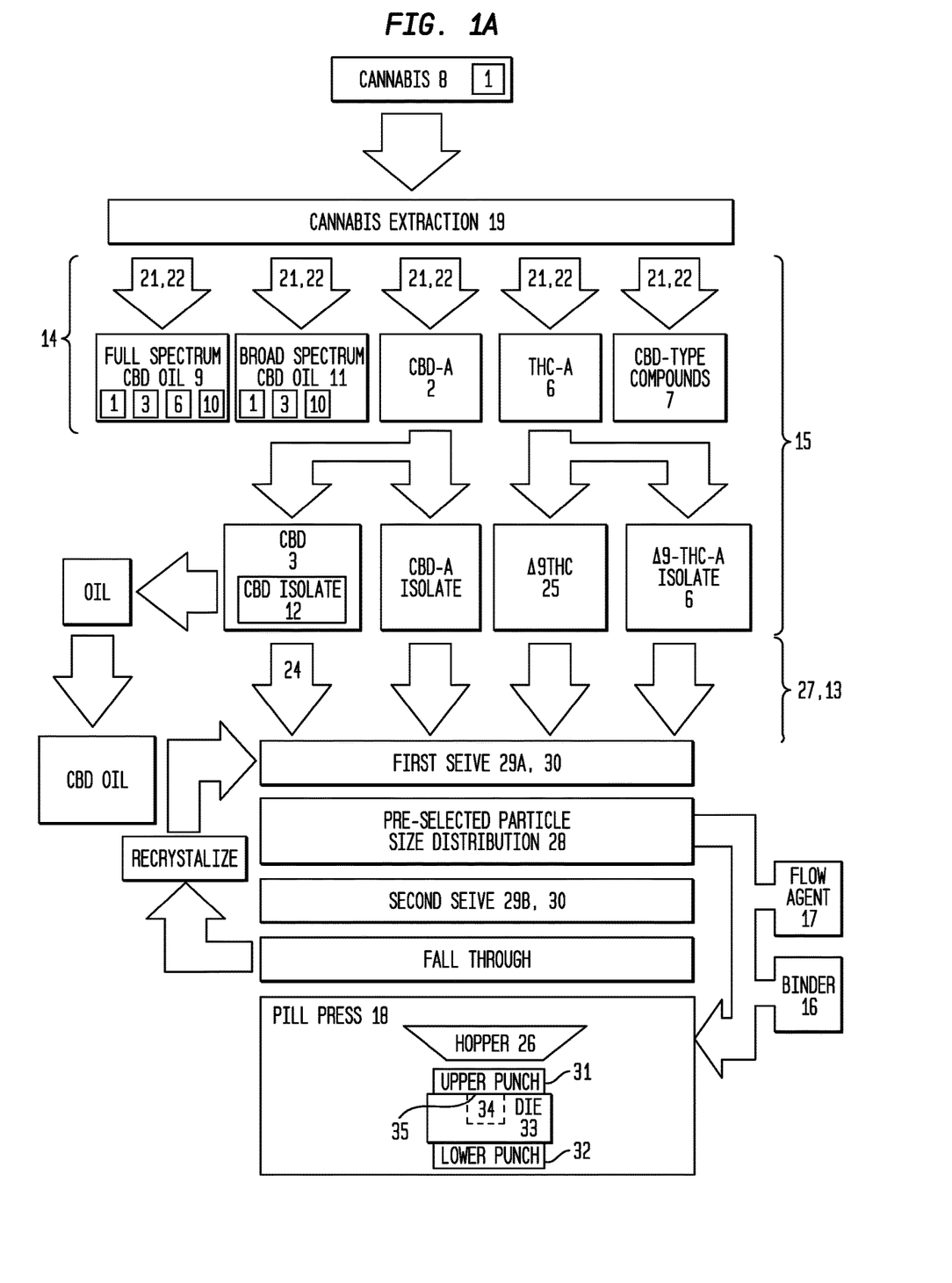
FIG. 1A is a block flow diagram of a particular method of making a dosage form including an amount of cannabinoid pressed into a tablet.
Figure 1B:
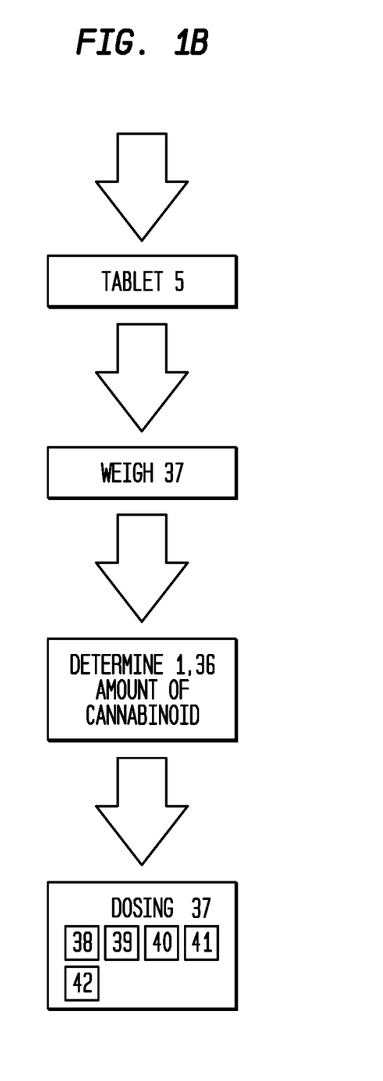
FIG. 1B is a continuation of the block flow diagram of FIG. 1A of making a dosage form including an amount of cannabinoid pressed into a tablet.
Figure 2:
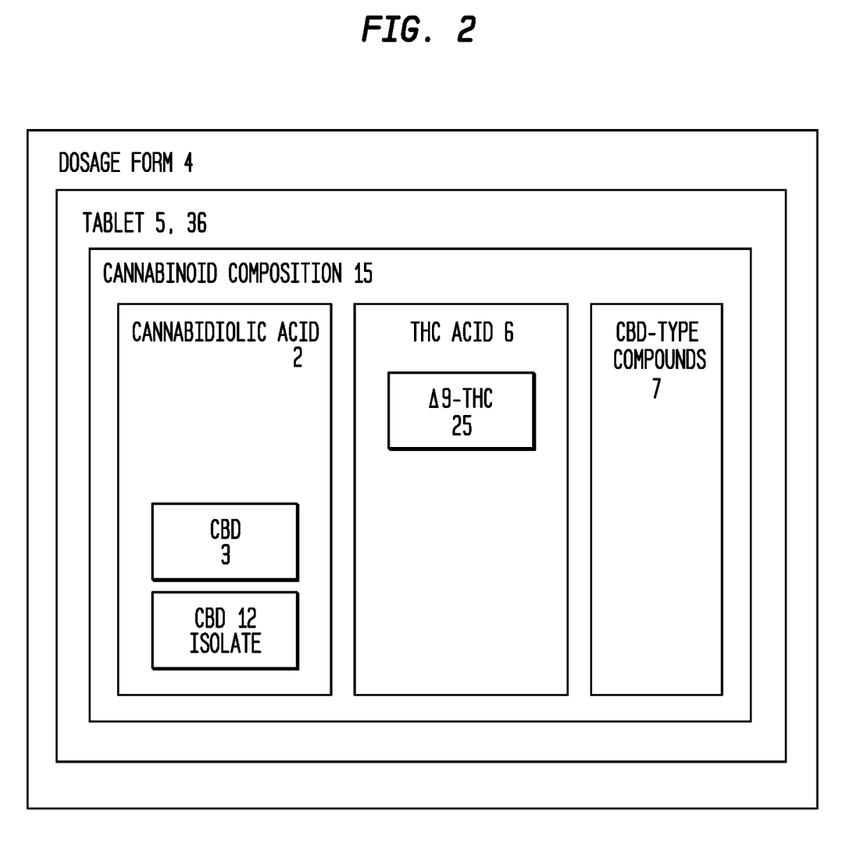
FIG. 2 is a block diagram of particular embodiments of a dosage form including an amount of cannabinoid pressed into a tablet.

Referring generally to FIGS. 1A, 1B and 2, embodiments of a dosage form (4) including, consisting essentially of, or consisting of an amount of cannabinoid (1), cannabidiolic acid (2) or cannabidiol (3), or combinations thereof. In particular embodiments, the dosage form (4) comprises a tablet (5) including, consisting essentially of, or consisting of an amount of cannabinoid (1), cannabidiolic acid (2) or cannabidiol (3).

The term "tablet," as used herein, means a compressed or molded solid substance or combination of substances, and without limitation to the breadth of the foregoing, a tablet (5) can comprise compressed or molded substance(s) containing an amount of cannabinoid (1), cannabidiolic acid (2), cannabidiol (3) or combinations thereof, and in particular embodiments a tablet (5) comprising only, consistent essentially of, or consisting of compressed or molded cannabidiolic acid (2) or cannabidiol (3), and in particular embodiments comprising only, consisting essentially of, or consisting of cannabidiol (3).

The term "cannabinoid (1)" as used herein means cannabigerol-type compounds whether obtained from *Cannabis* plant or chemically synthesized, their derivatives, enantiomers, or isotopes, and without limitation to the breadth of the forgoing, includes as illustrative examples: cannabigerolic acid, tetrahydrocannabinolic acid or cannabidiolic acid.

The term "Δ9-tetrahydrocannabinol (25)" (CAS Number 1972-08-3) ("THC") as used herein means decarboxylated tetrahydrocannabinolic acid (6) (THC-A) having a molecular formula of $C_{21}H_{30}O_2$ and a molecular weight of 314.47 grams per mole, its derivatives, enantiomers, and isotopes. Δ9-tetrahydrocannabinol can be generated by exposure of tetrahydrocannabinolic acid (6) to heat by any one or a combination of smoking, cooking, vaporization, or alkaline conditions or light.

The term "cannabidiol (3)" (CAS Number 13956-29-1) ("CBD") as used herein, means decarboxylated cannabidiolic acid (2)("CBD-A") having a molecular formula of $C_{21}H_{30}O_2$ and a molecular weight of 314.464 grams per mole, its derivatives, enantiomers, and isotopes.

However, the illustrative examples described are not intended to preclude embodiments which include, consistent essentially of, or consist of other cannabidiol-type compounds (7), as illustrative examples: cannabidivarinic acid, cannabidiorcol, cannabidiol-C4, cannabidivarin, cannabidiol monomethyl ether, and cannabinodivarin, whether naturally made or synthetically made.

With the legalization of *Cannabis* (8) in several states and the emerging promise of cannabinoids (1) obtained from various species of *Cannabis* (8) as natural pharmaceutical agents, methods of delivery of *Cannabis* cannabinoids (1) are of interest. Cannabinoids (1) obtained or extracted from various species of *Cannabis* (8) or derived therefrom, or otherwise chemically synthesized, have been shown to be effective to alleviate symptoms of or to treat a wide variety of conditions, including as illustrative examples: glaucoma, epilepsy, Dravet's syndrome, cancer, anxiety, Alzheimer's, muscle spasms, pain from multiple sclerosis, inflammatory bowel disease, pain from arthritis, lupus, Parkinson's disease, post-traumatic stress disorder, pain and nausea accompanying chemotherapy, anorexia, and drug dependency and withdrawal.

*Cannabis* cannabinoids (1), or derivatives thereof, are often administered or delivered by ingestion as a component of an edible composition, whether as solids or liquids, or by inhalation of smoke from burning parts of the *Cannabis* plant (8) (such as stem, leaves or flowers) or the extracts or derivates obtained therefrom.

Cannabidiol (3) has been shown to be pharmaceutically effective to alleviate the symptoms or treat certain disorders such as chronic pain, arthritis, multiple sclerosis, fibromyalgia, anxiety, insomnia, epilepsy, seizures, and cancer. In particular, CBD can have neuroprotective, antiepileptic, hypoxia-ischemia, anxiolytic, antipsychotic, analgesic, anti-inflammatory, anti-asthmatic, anticonvulsant, anti-emetic, anti-oxidant, and antitumor properties.

One attractive quality of CBD (3) can be that formulations of CBD (3) do not include noticeable amounts of the psychotropic chemical delta-9-tetrahydrocannabinol (THC) (25). Thus, users of CBD preparations may not experience significant psychotropic effects when using CBD preparations. CBD preparations can be procured in generally three forms of preparation. First, CBD can be obtained as a component of a full spectrum CBD oil (9), which contains CBD (3) well as other cannabinoids (1), terpenes (10), and trace amounts of THC (25). Second, CBD (3) can be obtained as a component of a broad spectrum CBD oil (11), which contains CBD (3) as well as other cannabinoids (1), terpenes (10), and negligible to no amounts of THC (25). Third, the CBD (3) can be obtained as CBD isolate (12), a crystallized form of CBD (3), which contains only CBD (3) at a certain level of purity with trace, negligible, or de minimis amounts of THC (25). CBD Isolate (12) can have a pre-determined purity level (13), and in particular embodiments the purity level (13) can be about or greater than 99% CBD (3).

In order to administer or deliver a pre-determined amount of CBD (3) (also referred to as a "dose"), the amount of CBD (3) in a composition, or portions thereof, must be accurately determined to allow the composition to be divided into doses. CBD compositions (14) can be difficult to divide into doses. For example, 100 mg of a full spectrum CBD oil (9) can have a CBD purity level (13) of 80%, meaning 80 mg of CBD (3) can be present in 100 mg of full spectrum CBD oil (9). However, dividing the full spectrum CBD oil (9) into ten equal portions may not yield ten, 10 mg doses of CBD (3) because the allocated portions may not have equal purity levels (13) of the CBD (3). The difference in the purity level (13) of CBD (3) in each portion may be the result of ineffective mixing of the full spectrum CBD oil (9) or other separation of CBD (3) within the full spectrum CBD oil (9) which affords a heterogenous mixture. Thus, it may not be possible to divide a CBD composition (14) into doses and correspondingly a user may not be able to administer or deliver a dose of CBD (3).

Embodiments, of the invention can provide accurate and precise dosage forms (4) by compressing or molding a homogenous cannabinoid composition (15) into a tablet (5). Administration of the tablet (5) correspondingly provides accurate and precise dosing. As an illustrative example, a homogenous CBD composition (14) having a known purity level (13) can be compressed into a tablet (5) and can afford a known purity level (13) of CBD (3) to afford a known quantity of CBD (3) based on total tablet weight. For example, a 10.0 mg tablet (5) containing CBD (3) having a purity level (13) of 90% contains 9.0 mg of CBD (3). Thus, an exact dosage (36) of CBD (3) can be administered.

Moreover, a tablet of a homogenous cannabinoid composition (15) can be divided into fractions, whereby half of a 10 mg tablet (5) of a homogenous cannabinoid composition (15) having 99% purity can contain 4.95 mg of cannabinoid composition (15). In particular embodiments, a tablet containing a homogenous CBD composition (14) of a known CBD (3) purity level (13), can permit administration of accurate dosages to predictably treat disorders or alleviate disorder symptoms. In particular embodiments, the homogenous cannabinoid composition (15) can comprise only, consist essentially of, or consist of an amount of CBD (3) of a known purity level (13), or in particular embodiments, the CBD (3) of known purity level (13) can further include a sufficient amount of a binder (16) or a flow agent (17) to allow production of the tablets (5) with a pill press (18) which in particular embodiments can comprise a conventional pill press.

With reference primarily to FIGS. 1A and 1B, Cannabinoids (1), and as an illustrative example applicable to other cannabinoid compounds, CBD-A (2) or CBD (3) can be extracted (19) from numerous species of *Cannabis* plants (8) using various extraction (19) methods including $CO_2$ extraction, olive oil extraction, dry ice extraction, solvent extraction, and other similar or equivalent methods of extraction. Without preclusive effect and by way of example, extraction (19) of CBD-A (6) or CBD (3) from *Cannabis* (8) can be achieved using $CO_2$ extraction as described in EP 3274321 to Eiroa Martinez et al., U.S. Pat. No. 10,092,855 to Chess, U.S. Pat. No. 9,044,390 to Speier, and U.S. Pat. No. 9,186, 386 to Speier, each hereby incorporated by reference herein. In general, $CO_2$ extraction includes the steps of obtaining *Cannabis* plant material (8) and performing $CO_2$ extraction using $CO_2$ as a solvent to collect a fraction containing a crude extract (20) of CBD-A (2) or CBD (3). The crude extract (20) of CBD-A (2) or CBD (3) can then be refined (21) through further procedures such as filtration or thin film evaporation. In particular embodiments, the refined extract (23) of CBD-A (2) or CBD (3) can then be dissolved in a solvent which can be induced to yield CBD crystals (24) (also referred to as "crystalline CBD").

Generally, CBD isolate (12) can be obtained in crystalline form. Full spectrum CBD oil (9) and broad spectrum CBD oil (11) can be obtained in oil (liquid) form. The oil form of full spectrum CBD (9) or broad spectrum CBD (11) can undergo filtration (21) to further purify the CBD (3) in the oil. Further, the full spectrum or broad spectrum CBD (9)(11) can be obtained in crystalline form.

Crystalline CBD (24), whether derived from full spectrum CBD oil (9), broad spectrum CBD oil (11), or CBD isolate (12) can be utilized in the formation of embodiments of CBD tablets (5). CBD (3) used in preparing embodiments of the CBD tablet (5) can have a pre-determined purity level (13). The term "purity level" means the total weight of CBD (3) present in a CBD composition (14) in relation to the total weight of the CBD composition (14), expressed as a percentage. As an illustrative example, a 50% purity level (13) of CBD (3) in a 100 mg tablet (5) of CBD composition contains 50 mg of CBD (3). By knowing the purity level (13) of the CBD (3) being pressed into a tablet (5) and the weight of the tablet (5), a user can determine the amount of CBD (3) being ingested, or the CBD dose.

In particular embodiments, an amount of a flow agent (17) can, but need not necessarily, be admixed with the CBD (3). A flow agent (17) admixed with the active ingredients can assist in movement of the CBD (3) in a pill press (18). A sufficient amount of flow agent (17) can be admixed to allow movement of the CBD (3) from the pill press hopper (26) into the press portions of the pill press (18). The flow agent (17) can be compressed into the tablet (5) along with CBD (3). In particular embodiments, the flow agent (17) can be dicalcium phosphate; however, other flow agents (17) including cellulose or silicate may also be utilized.

In particular embodiments, an amount of a binder (16) can, but need not necessarily, be admixed with the CBD (3) and the flow agent (17), if present. Binders (16), also referred to as binding agents, assist in the compression and resultant adhesion of the particles contained in the tablet (5) to promote the compressed particles remaining in tablet form as opposed to crumbling after pressing. As illustrative examples, the binder (16) be can one or more of starch, polyethylene glycol, cellulose, or the like.

In particular embodiments, the cannabinoid (1) purity level (13) can occur in a range of about 80.0% to about 99.9%. In particular embodiments, the amount of cannabinoid (1) can have a purity level (13) in a range selected from the group consisting of: about 81.0% to about 83%, about 82.0% to about 84%, about 83.0% to about 85%, about 84.0% to about 86%, about 85.0% to about 87%, about 86.0% to about 88%, about 87.0% to about 89%, about 88.0% to about 90%, about 89.0% to about 91%, about 90.0% to about 92%, about 91.0% to about 93%, about 92.0% to about 94%, about 93.0% to about 95%, about 94.0% to about 96%, about 95.0% to about 97%, about 96.0% to about 98%, about 97.0% to about 99%, about 98.0% to about 99.5%, or combinations thereof. In particular embodiments, the purity level (13) of the amount of cannabinoid (1) can be about 99.9%.

In particular embodiments, the dosage form (4) can include only, or consist essentially of, or consist of an amount of CBD (3) pressed into a tablet (5). Thus, CBD crystals (24) can be used without the addition of binders (16) or flow agents (17). The purity level (13) of the CBD crystals (24) can be about 90% to about 99.9%. In particular embodiments, the purity level (13) of the CBD crystals (24) can occur within a range selected from the group consisting of: about 90.5% to about 91.5%, about 91% to about 92%, about 91.5% to about 92.5%, about 92% to about 93%, about 92.5% to about 93.5%, about 93% to about 94%, about 93.5% to about 94.5%, about 94% to about 95%, about 94.5% to about 95.5%, about 95% to about 96%, about 95.5% to about 96.5%, about 96% to about 97%, about 96.5% to about 97.5%, about 97% to about 98%, about 97.5% to about 98.5%, about 98% to about 99%, about 98.5% to about 99.5%, or combinations thereof. In particular embodiments, the dosage form (4) can include an amount of CBD (3) of at least 90% purity. In further particular embodiments, the dosage form (4) can include an amount of CBD (3) of at least 95% purity. In yet further particular embodiments, the dosage form (4) can include an amount of CBD (3) of at least 99% purity.

Again, primarily referring to FIGS. 1A and 1B, without preclusive effect to the foregoing, it has been discovered that obtaining cannabinoid crystals (27) within a pre-selected particle size distribution range (28) can permit embodiments of the tablet (5) to be pressed or formed by operation of a pill press (18) without the need or minimizing the need for flow agents (17) or binders (16). To achieve the particle size distribution range (28) in an amount of cannabinoid crystals (27), and as an illustrative example, cannabinoid crystals (27) can be crushed and sifted through a series of sieves. The upper and lower boundary of the particle size distribution range (28) can be achieved by utilizing a pair of sieves (29A)(29B) having a mesh size (30) capable of entrapping cannabinoid (1) particles of the required particle size distribution range (28) between the pair of sieves (29A)(29B) and omitting particles of cannabinoid crystals (27) or crystalline CBD (24) outside of the required particle size distribution range (28) from being entrained between the pair of sieves (29A)(29B). The portion of cannabinoid crystals (27) which does not fall through the first sieve (29A) having a mesh size (30) affording an open area defining the upper boundary of the pre-selected upper particle size distribution range (28) can be further processed into particles of lesser size and reintroduced to the first sieve (29A). The portion of cannabinoid crystals (27) or crystalline CBD (24) which flowed through the first sieve (29A) can then be introduced into a second sieve (29B) affording an open area defining the lower boundary of the pre-selected lower particle size distribution range (28), where the cannabinoid crystals (27) or crystalline CBD (24) which flow through the second sieve (29B) are less than the lower boundary of the particle size distribution range (28). The particles of cannabinoid crystals (27) or crystalline CBD (24) which did not flow through the second sieve (29B) will have a greater size than the lower boundary of the particle size distribution range (28) and a lesser size than the upper boundary of the particle size distribution range (28).

By way of illustrative example, in generating the pre-selected particle size distribution range (28) of crystalline CBD (24), a first sieve (29A) having a mesh size (30) of about 2000 microns can permit crystalline CBD (24) particles having a size of about 2000 microns and less to flow through the first sieve (29A) and be separated from crystalline CBD (24) particles having a particle size greater than about 2000 microns. The portion of crystalline CBD (24) particles which flowed through the first sieve (29A) can then be flowed through a second sieve (29B) having a mesh size (30) of about 20 microns. The crystalline CBD (25) particles which flowed through the second sieve (29B) have a lesser size than 20 microns. The crystalline CBD (24) particles remaining in the second sieve (29B) can have a greater size than 20 microns or about 20 microns, but less than or about 2000 microns, thereby imparting a particle size distribution range (28) of about 20 microns to about 2000 microns.

In particular embodiments, the particle size distribution range (28) can be a range of about 20 microns to about 2000 microns. In particular embodiments, the particle size distribution range (28) can be a range of about 25 microns to about 1250 microns. In particular embodiments, the particle size distribution range (28) is selected from the group consisting of: about 22.5 microns to about 2000 microns, about 50 microns to about 2000 microns, about 75 microns to about 2000 microns, about 100 microns to about 2000 microns, about 125 microns to about 2000 microns, about 150 microns to about 2000 microns, about 175 microns to about 2000 microns, about 200 microns to about 2000 microns, about 225 microns to about 2000 microns, about 250 microns to about 2000 microns, about 275 microns to about 2000 microns, about 300 microns to about 2000 microns, about 325 microns to about 2000 microns, about 350 microns to about 2000 microns, about 375 microns to about 2000 microns, about 400 microns to about 2000 microns, about 425 microns to about 2000 microns, about 450 microns to about 2000 microns, about 475 microns to about 2000 microns, about 500 microns to about 2000 microns, about 525 microns to about 2000 microns, 550 microns to about 2000 microns, about 575 microns to about 2000 microns, about 600 microns to about 2000 microns, about 625 microns to about 2000 microns, about 650 microns to about 2000 microns, about 675 microns to about 2000 microns, about 700 microns to about 2000 microns, about 725 microns to about 2000 microns, about 750 microns to about 2000 microns, about 775 microns to about 2000 microns, about 800 microns to about 2000 microns, about 825 microns to about 2000 microns, about 850 microns to about 2000 microns, about 875 microns to about 2000 microns, about 900 microns to about 2000 microns, about 925 microns to about 2000 microns, about 950 microns to about 2000 microns, about 975 microns to about 2000 microns, about 1000 microns to about 2000 microns, about 1025 microns to about 2000 microns, about 1050 microns to about 2000 microns, about 1075 microns to about 2000 microns, about 1100 microns to about 2000 microns, about 1125 microns to about 2000 microns, about 1150 microns to about 2000 microns, about 1175 microns to about 2000 microns, about 1200 microns to about 2000 microns, about 1225 microns to about 2000 microns, about 1250 microns to about 2000 microns, about 1275 microns to about 2000 microns, about 1300 microns to about 2000 microns, about 1325 microns to about 2000 microns, about 1350 microns to about 2000 microns, about 1375 microns to about 2000 microns, about 1400 microns to about 2000 microns, about 1425 microns to about 2000 microns, about 1450 microns to about 2000 microns, about 1475 microns to about 2000 microns, about 1500 microns to about 2000 microns, about 1525 microns to about 2000 microns, about 1550 microns to about 2000 microns, about 1575 microns to about 2000 microns, about 1600 microns to about 2000 microns, about 1625 microns to about 2000 microns, about 1650 microns to about 2000 microns, about 1675 microns to about 2000 microns, about 1700 microns to about 2000 microns, about 1725 microns to about 2000 microns, about 1750 microns to about 2000 microns, about 1775 microns to about 2000 microns, about 1800 microns to about 2000 microns, about 1825 microns to about 2000 microns, about 1850 microns to about 2000 microns, about 1875 microns to about 2000 microns, about 1900 microns to about 2000 microns, about 1925 microns to about 2000 microns, about 1950 microns to about 2000 microns, about 1975 microns to about 2000 microns, or combinations thereof.

In particular embodiments, the particle size distribution range (28) is selected from the group consisting of: about 20 microns to about 1975 microns, about 20 microns to about 1950 microns, about 20 microns to about 1925 microns, about 20 microns to about 1900 microns, about 20 microns to about 1875 microns, about 20 microns to about 1850 microns, about 20 microns to about 1825 microns, about 20 microns to about 1800 microns, about 20 microns to about 1775 microns, about 20 microns to about 1750 microns, about 20 microns to about 1725 microns, about 20 microns to about 1700 microns, about 20 microns to about 1675 microns, about 20 microns to about 1650 microns, about 20 microns to about 1625 microns, about 20 microns to about 1600 microns, about 20 microns to about 1575 microns, about 20 microns to about 1550 microns, about 20 microns to about 1525 microns, about 20 microns to about 1500 microns, about 20 microns to about 1475 microns, about 20 microns to about 1450 microns, about 20 microns to about 1425 microns, about 20 microns to about 1400 microns, about 20 microns to about 1375 microns, about 20 microns to about 1350 microns, about 20 microns to about 1325 microns, about 20 microns to about 1300 microns, about 20 microns to about 1275 microns, about 20 microns to about 1250 microns, about 20 microns to about 1225 microns, about 20 microns to about 1200 microns, about 20 microns to about 1175 microns, about 20 microns to about 1150 microns, about 20 microns to about 1125 microns, about 20 microns to about 1100 microns, about 20 microns to about 1075 microns, about 20 microns to about 1050 microns, about 20 microns to about 1025 microns, about 20 microns to about 1000 microns, about 20 microns to about 975 microns, about 20 microns to about 950 microns, about 20 microns to about 925 microns, about 20 microns to about 900 microns, about 20 microns to about 875 microns, about 20 microns to about 850 microns, about 20 microns to about 825 microns, about 20 microns to about 800 microns, about 20 microns to about 775 microns, about 20 microns to about 750 microns, about 20 microns to about 725 microns, about 20 microns to about 700 microns, about 20 microns to about 675 microns, about 20 microns to about 650 microns, about 20 microns to about 625 microns, about 20 microns to about 600 microns, about 20 microns to about 575 microns, about 20 microns to about 550 microns, about 20 microns to about 525 microns, about 20 microns to about 500 microns, about 20 microns to about 475 microns, about 20 microns to about 450 microns, about 20 microns to about 425 microns, about 20 microns to about 400 microns, about 20 microns to about 375 microns, about 20 microns to about 350 microns, about 20 microns to about 325 microns, about 20 microns to about 300 microns, about 20 microns to about 275 microns, about 20 microns to about 250 microns, about 20 microns to about 225 microns, about 20 microns to about 200 microns, about 20 microns to about 175 microns, about 20 microns to about 150 microns, about 20 microns to about 125 microns, about 20 microns to about 100 microns, about 20 microns to about 75 microns, about 20 microns to about 50 microns, about 20 microns to about 25 microns, or combinations thereof.

In particular embodiments, the particle size distribution range (28) is selected from the group consisting of: about 22.5 microns to about 75 microns, about 50 microns to about 100 microns, about 75 microns to about 125 microns, about 100 microns to about 150 microns, about 125 microns to about 175 microns, about 150 microns to about 200 microns, about 175 microns to about 225 microns, about 200 microns to about 250 microns, about 225 microns to about 275 microns, about 250 microns to about 300 microns, about 275 microns to about 325 microns, about 300 microns to about 350 microns, about 325 microns to about 375 microns, about 350 microns to about 400 microns, about 375 microns to about 425 microns, about 400 microns to about 450 microns, about 425 microns to about 475 microns, about 450 microns to about 500 microns, about 475 microns to about 525 microns, about 500 microns to about 550 microns, about 525 microns to about 575 microns, about 550 microns to about 600 microns, about 575 microns to about 625 microns, about 600 microns to about 650 microns, about 625 microns to about 675 microns, about 650 microns to about 700 microns, about 675 microns to about 725 microns, about 700 microns to about 750 microns, about 725 microns to about 775 microns, about 750 microns to about 800 microns, about 775 microns to about 825 microns, about 800 microns to about 850 microns, about 825 microns to about 875 microns, about 850 microns to about 900 microns, about 875 microns to about 925 microns, about 900 microns to about 950 microns, about 925 microns to about 975 microns, about 950 microns to about 1000 microns, about 975 microns to about 1025 microns, about 1000 microns to about 1050 microns, about 1025 microns to about 1075 microns, about 1050 microns to about 1100 microns, about 1075 microns to about 1125 microns, about 1100 microns to about 1150 microns, about 1125 microns to about 1175 microns, about 1150 microns to about 1200 microns, about 1175 microns to about 1225 microns, about 1200 microns to about 1250 microns, about 1225 microns to about 1275 microns, about 1250 microns to about 1300 microns, about 1275 microns to about 1325 microns, about 1300 microns to about 1350 microns, about 1325 microns to about 1375 microns, about 1350 microns to about 1400 microns, about 1375 microns to about 1425 microns, about 1400 microns to about 1450 microns, about 1425 microns to about 1475 microns, about 1450 microns to about 1500 microns, about 1475 microns to about 1525 microns, about 1500 microns to about 1550 microns, about 1525 microns to about 1575 microns, about 1550 microns to about 1600 microns, about 1575 microns to about 1625 microns, about 1600 microns to about 1650 microns, about 1625 microns to about 1675 microns, about 1650 microns to about 1700 microns, about 1675 microns to about 1725 microns, about 1700 microns to about 1750 microns, about 1725 microns to about 1775 microns, about 1750 microns to about 1800 microns, about 1775 microns to about 1825 microns, about 1800 microns to about 1850 microns, about 1825 microns to about 1875 microns, about 1850 microns to about 1900 microns, about 1875 microns to about 1925 microns, about 1900 microns to about 1950 microns, about 1925 microns to about 1975 microns, about 1950 microns to about 1995 microns, or combinations thereof.

Again referring primarily to FIGS. 1A and 1B, particular methods of making a tablet (5) dosage form (4) including an amount of cannabinoid (1), and in particular, CBD (3), includes one or more of obtaining an amount of cannabinoid crystals (27), which in particular embodiments can further include cannabinoid crystals (27) having a pre-selected purity level (13) or a particle size distribution range (28), or both; disposing an amount of cannabinoid crystals (27), and in particular crystalline CBD (24), in a pill press (18), and operating the pill press (18) to form one or more cannabinoid tablets (5), and in the illustrative example below, CBD tablets (5).

The general components of a pill press (18) include a hopper (26) which receives the CBD crystals (24) to be pressed into a tablet (5), a lower and an upper punch (31)(32), and a die (33). The CBD crystals (24) to be pressed into a tablet (5) can be metered from the hopper (26) into a cavity (34) formed by the lower punch (31) and the die (33). In operation, the lower punch (31) can be lowered within the die (33) to create a cavity (34). The height of the lower punch (31), can be adjusted to either increase or decrease the depth of the cavity (34). The CBD crystals (24) to be pressed into a tablet (5) can be metered from the hopper (26) into the cavity (34). Any excess amount of CBD crystals (24) to be pressed into a tablet (5) can be scraped from the opening (35) of the cavity (34). The upper punch (32) can then be brought down and into the cavity (34), thereby imparting compressive force to the CBD crystals (24) to be pressed into a tablet (5). The upper punch (32) is then retracted as the lower punch (31) is raised to eject the compressed and formed tablet (5) of CBD (3)(12) from the cavity (34). A particular example of a pill press (18) is the TDP-5 Pill Press by LFA Machines Oxford Ltd.; however other pill press (18) embodiments are contemplated and may be used.

The method of making the dosage form (4) including an amount of CBD (3) pressed into a tablet (5) can further include weighing (37) the CBD tablets (5) produced by the pill press (18), determining the average weight of the tablets (5), and adjusting the fill depth, or height of the cavity (34) created by the die (33) and lower punch (31), to increase or decrease the average weight of the tablets (5).

As an illustrative example, the pill press (18) can be operated to produce 20 mg CBD tablets (5) containing only, consisting essentially of, or consisting of an amount of CBD (3) having a purity level (13) of about 99.9% without the addition of any binders (16) or flow agents (17). The particle size distribution range (28) of the amount of CBD (3) can occur in a range of about 25 microns to about 1250 microns. Ten tablets (5) may be selected from those produced by the pill press (18) and weighed. The weight of the ten tablets (5), divided by ten, produces the average weight of each tablet (5). If the weight is greater than 20 mg, the height of the cavity (34) may be decreased to lower the average weight of the tablet (5). If the weight is less than 20 mg, the height of the cavity (34) may be increased to increase the average weight of the tablet (5). If the weight is about 20 mg, then the amount of CBD (3) is about 19.98 mg per tablet (5).

In particular embodiments, the amount of cannabinoid (1), and in particular CBD (3), can be a pre-determined amount of cannabinoid (1) pressed into a tablet (5). The pre-determined amount of cannabinoid (1) can have a range of about 5 mg to about 1000 mg of cannabinoid (1) pressed into a tablet. In particular embodiments, the pre-determined amount of cannabinoid (1) can be selected from the group consisting of: about 6 mg to about 50 mg, about 25 mg to about 75 mg, about 50 mg to about 100 mg, about 75 mg to about 125 mg, about 100 mg to about 150 mg, about 125 mg to about 175 mg, about 150 mg to about 200 mg, about 175 mg to about 225 mg, about 200 mg to about 250 mg, about 225 mg to about 275 mg, about 250 mg to about 300 mg, about 275 mg to about 325 mg, about 300 mg to about 350 mg, about 325 mg to about 375 mg, about 350 mg to about 400 mg, about 375 mg to about 425 mg, about 400 mg to about 450 mg, about 425 mg to about 475 mg, about 450 mg to about 500 mg, about 475 mg to about 525 mg, about 500 mg to about 550 mg, about 525 mg to about 575 mg, about 550 mg to about 600 mg, about 575 mg to about 625 mg, about 600 mg to about 650 mg, about 625 mg to about 675 mg, about 650 mg to about 700 mg, about 675 mg to about 725 mg, about 700 mg to about 750 mg, about 725 mg to about 775 mg, about 750 mg to about 800 mg, about 775 mg to about 825 mg, about 800 mg to about 850 mg, about 825 mg to about 875 mg, about 850 mg to about 900 mg, about 875 mg to about 925 mg, about 900 mg to about 950 mg, about 925 mg to about 975 mg, about 950 mg to about 995 mg, or combinations thereof.

In further particular embodiments, the amount of cannabinoid (1), and in particular cannabidiol (3), can be a pre-determined amount of cannabinoid (1) pressed into a tablet (5). The pre-determined amount of cannabinoid (1) can have a range of about 5 mg to about 50 mg of cannabinoid (1) pressed into a tablet. In particular embodiments, the pre-determined amount of cannabinoid (1) can be selected from the group consisting of: about 6 mg to about 8 mg, about 7 mg to about 9 mg, about 8 mg to about 10 mg, about 9 mg to about 11 mg, about 10 mg to about 12 mg, about 11 mg to about 13 mg, about 12 mg to about 14 mg, about 13 mg to about 15 mg, about 14 mg to about 16 mg, about 15 mg to about 17 mg, about 16 mg to about 18 mg, about 17 mg to about 19 mg, about 18 mg to about 20 mg, about 19 mg to about 21 mg, about 20 mg to about 22 mg, about 21 mg to about 23 mg, about 22 mg to about 24 mg, about 23 mg to about 25 mg, about 24 mg to about 26 mg, about 25 mg to about 27 mg, about 26 mg to about 28 mg, about 27 mg to about 29 mg, about 28 mg to about 30 mg, about 29 mg to about 31 mg, about 30 mg to about 32 mg, about 31 mg to about 33 mg, about 32 mg to about 34 mg, about 33 mg to about 35 mg, about 34 mg to about 36 mg, about 35 mg to about 37 mg, about 36 mg to about 38 mg, about 37 mg to about 39 mg, about 38 mg to about 40 mg, about 39 mg to about 41 mg, about 40 mg to about 42 mg, about 41 mg to about 43 mg, about 42 mg to about 44 mg, about 43 mg to about 45 mg, about 44 mg to about 46 mg, about 45 mg to about 47 mg, about 46 mg to about 48 mg, about 47 mg to about 49 mg, or combinations thereof. In further particular embodiments, the pre-determined amount of cannabinoid (1) can be about 20 mg to about 30 mg. In yet further particular embodiments, the pre-determined amount of cannabinoid (1) can be about 25 mg.

Now referring primarily to FIG. 2, particular methods of using the tablet (5) can include obtaining one or more tablets (5), where the one or more tablets (5) include an amount of cannabinoid (1), and in particular cannabidiol (3), having a pre-selected purity level (13) and a pre-selected weight, determining the amount of cannabidiol (3) in the one or more tablets (5), determining a dosage (36) of the amount of cannabidiol (3), selecting one or more tablets (5) corresponding to the dosage (36), and consuming the one or more tablets (5). Determining the amount of cannabidiol (3) in each of the one or more tablets (5) can include multiplying the purity level (13) of the cannabidiol (3) in the tablet and the weight of the tablet (5) to determine the amount of cannabidiol (3) per tablet (5). By way of nonlimiting illustration, a tablet (5) can have an amount of cannabidiol (3) corresponding to a purity level (13) of 99% and weight of 10 mg. The amount of cannabidiol (3) in the tablet can be calculated to yield 9.9 mg of cannabidiol (3). The one or more tablets (5) can be consumed to deliver a desired amount of cannabidiol (3) by either consuming a portion of one tablet (5), one tablet (5), multiple tablets (5), one tablet (5) and a portion of a tablet (5), or multiple tablets (5) and a portion of a tablet (5). Each of the one or more tablets (5) can be a homogenous mixture, so that the tablets (5) can be mechanically divided into portions of tablets (5) having a correlating fraction of an amount of cannabidiol (3). Again, by way of nonlimiting example, one or more tablets (5) can have an amount of cannabidiol (3) corresponding to a purity level (13) of 99% and weight of 10 mg. The amount of cannabidiol (3) in the tablet (5) can be calculated to yield 9.9 mg of cannabidiol (3). To increase the dosage (36), two tablets (5) may be consumed for a total yield of 19.8 mg. Alternatively, one and a half tablets (5) may be consumed for a total yield of 14.85 mg. As a further alternative, one tablet (5) may be divided in half to yield 4.95 mg.

In further particular methods of using the tablet (5), the one or more tablets (5) can be dosed or consumed (37), whether orally (38), disposed in a fluid for imbibing (39), disposed in food for ingestion (40), or combined with an ointment or cream for topical application to a body (41). The tablets (5) may, but need not necessarily, be crushed into powder form prior to being disposed in a fluid or food (39)(40) or combined with an ointment or cream (41).

In particular methods, the one or more tablets (5) can be heated and the resulting vapor can be inhaled through the use of a vaporizing apparatus (42). Vaporizing apparatuses (42), in general, operate by including an atomizer, cartomizer, or clearomizer attached to a power source. The power source heats a heating element, such as a metal coil, in the atomizer, cartomizer, or clearomizer. The metal coil can be convectionally or conductionally coupled to one or more tablets (5) or other solid or liquid substances, or combinations thereof, contained in a load chamber of the atomizer, cartomizer, or clearomizer. The metal coil heats the tablet (5) or solid or liquid substance until the solid or liquid substance generates an inhalable vapor. The vapor can be inhaled from the atomizer through an exit port on the atomizer, cartomizer, or clearomizer. Nonlimiting examples of vaporizing apparatuses (42) can include, but are not limited to, pen vaporizers, pocket vaporizers, box mod vaporizers, desktop vaporizers, and table-top vaporizers. A specific nonlimiting example of a vaporizing apparatus (42) is the Yocan® Evolve Plus Vaporizer which includes an atomizer electrically coupled to a rechargeable battery.

As can be easily understood from the foregoing, the basic concepts of the present invention may be embodied in a variety of ways. The invention involves numerous and varied embodiments of a cannabidiol tablet and methods for making and using such cannabidiol tablet including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "press" should be understood to encompass disclosure of the act of "pressing"—whether explicitly discussed or not—and, conversely, were there effectively disclosure of the act of "pressing", such a disclosure should be understood to encompass disclosure of a "press" or even a "means for pressing." Such alternative terms for each element or step are to be understood to be explicitly included in the description.

In addition, as to each term used, it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the cannabidiol tablet herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A dosage form, consisting of cannabigerol isolate crystals, cannabinol isolate crystals, or Δ9-tetrahydrocannabinol isolate crystals each having a purity of at least 90% and a particle size of about 200 microns to about 600 microns, each of said cannabigerol isolate crystals, said cannabinol isolate crystals, or said Δ9-tetrahydrocannabinol isolate crystals pressed into a tablet.

2. The dosage form of claim 1, wherein said purity is selected from the group consisting of: about 91.0% to about 93%, about 92.0% to about 94%, about 93.0% to about 95%, about 94.0% to about 96%, about 95.0% to about 97%, about 96.0% to about 98%, about 97.0% to about 99%, about 98.0% to about 99.5%, or combinations thereof.

3. The dosage form of claim 1, wherein said cannabigerol isolate crystals, said cannabinol isolate crystals, or said Δ9-tetrahydrocannabinol isolate crystals pressed into said tablet having a tablet weight of about 5 mg to about 1000 mg.

4. The dosage form of claim 3, wherein said tablet weight is selected from the group consisting of: about 6 mg to about 50 mg, about 25 mg to about 75 mg, about 50 mg to about 100 mg, about 75 mg to about 125 mg, about 100 mg to about 150 mg, about 125 mg to about 175 mg, about 150 mg to about 200 mg, about 175 mg to about 225 mg, about 200 mg to about 250 mg, about 225 mg to about 275 mg, about 250 mg to about 300 mg, about 275 mg to about 325 mg, about 300 mg to about 350 mg, about 325 mg to about 375 mg, about 350 mg to about 400 mg, about 375 mg to about 425 mg, about 400 mg to about 450 mg, about 425 mg to about 475 mg, about 450 mg to about 500 mg, about 475 mg to about 525 mg, about 500 mg to about 550 mg, about 525 mg to about 575 mg, about 550 mg to about 600 mg, about 575 mg to about 625 mg, about 600 mg to about 650 mg, about 625 mg to about 675 mg, about 650 mg to about 700 mg, about 675 mg to about 725 mg, about 700 mg to about 750 mg, about 725 mg to about 775 mg, about 750 mg to about 800 mg, about 775 mg to about 825 mg, about 800 mg to about 850 mg, about 825 mg to about 875 mg, about 850 mg to about 900 mg, about 875 mg to about 925 mg, about 900 mg to about 950 mg, about 925 mg to about 975 mg, about 950 mg to about 995 mg, or combinations thereof.

5. The dosage form of claim 3, wherein said tablet weight is selected from the group consisting of: about 6 mg to about 8 mg, about 7 mg to about 9 mg, about 8 mg to about 10 mg, about 9 mg to about 11 mg, about 10 mg to about 12 mg, about 11 mg to about 13 mg, about 12 mg to about 14 mg, about 13 mg to about 15 mg, about 14 mg to about 16 mg, about 15 mg to about 17 mg, about 16 mg to about 18 mg, about 17 mg to about 19 mg, about 18 mg to about 20 mg, about 19 mg to about 21 mg, about 20 mg to about 22 mg, about 21 mg to about 23 mg, about 22 mg to about 24 mg, about 23 mg to about 25 mg, about 24 mg to about 26 mg, about 25 mg to about 27 mg, about 26 mg to about 28 mg, about 27 mg to about 29 mg, about 28 mg to about 30 mg, about 29 mg to about 31 mg, about 30 mg to about 32 mg, about 31 mg to about 33 mg, about 32 mg to about 34 mg, about 33 mg to about 35 mg, about 34 mg to about 36 mg, about 35 mg to about 37 mg, about 36 mg to about 38 mg, about 37 mg to about 39 mg, about 38 mg to about 40 mg, about 39 mg to about 41 mg, about 40 mg to about 42 mg, about 41 mg to about 43 mg, about 42 mg to about 44 mg, about 43 mg to about 45 mg, about 44 mg to about 46 mg, about 45 mg to about 47 mg, about 46 mg to about 48 mg, about 47 mg to about 49 mg, or combinations thereof.

6. The dosage form of claim 3, wherein said tablet weight is about 20 mg to about 30 mg.

7. The dosage form of claim 6, wherein said tablet weight is about 25 mg.

8. The dosage form of claim 1, wherein said particle size is selected from the group consisting of: 225 micron to about 275 micron, 250 micron to about 300 micron, about 275 microns to about 325 microns, about 300 microns to about 350 microns, about 325 microns to about 375 microns, about 350 microns to about 400 microns, about 375 microns to about 425 microns, about 400 microns to about 450 microns, about 425 microns to about 475 microns, about 450 microns to about 500 microns, about 475 microns to about 525 microns, about 500 microns to about 550 microns, about 525 microns to about 575 microns, or combinations thereof.

\* \* \* \* \*